United States Patent
Fehr et al.

(10) Patent No.: US 9,248,009 B2
(45) Date of Patent: Feb. 2, 2016

(54) MEDICAL CLEANING KIT

(75) Inventors: Daniel Fehr, Zürich (CH); Roland Herzog, Fislisbach (CH); S. Petter Lyngstadaas, Nesoddtangen (NO); Johan Caspar Wohlfahrt, Oslo (NO)

(73) Assignee: Straumann Holding AG, Basel (CH)

( * ) Notice: Subject to any disclaimer, the term of this patent is extended or adjusted under 35 U.S.C. 154(b) by 0 days.

(21) Appl. No.: 13/322,610

(22) PCT Filed: Jun. 3, 2010

(86) PCT No.: PCT/EP2010/057786
§ 371 (c)(1),
(2), (4) Date: Feb. 10, 2012

(87) PCT Pub. No.: WO2010/139762
PCT Pub. Date: Dec. 9, 2010

(65) Prior Publication Data

US 2012/0129129 A1 May 24, 2012

(30) Foreign Application Priority Data

Jun. 3, 2009 (SE) ...................................... 0900764

(51) Int. Cl.
*A61C 5/00* (2006.01)
*A61C 19/06* (2006.01)
(Continued)

(52) U.S. Cl.
CPC ................. *A61C 19/063* (2013.01); *A46B 3/18* (2013.01); *A46D 1/00* (2013.01); *A46D 1/0207* (2013.01); *A61C 3/005* (2013.01); *A61C 5/02* (2013.01); *A61C 8/00* (2013.01)

(58) Field of Classification Search
CPC ......... A46B 3/18; A46D 1/00; A46D 1/0207; A61C 5/02; A61C 3/005; A61C 8/00; A61C 19/063
USPC ........ 433/216, 102, 80–82, 89, 103; 103/329, 103/309, 321, 333, 224; 15/167.1, 182, 15/206, 207, 207.2; 401/291; 604/22, 264, 604/266, 267; 601/142, 162; 132/329, 309, 132/321, 333, 224

See application file for complete search history.

(56) References Cited

U.S. PATENT DOCUMENTS 4,060,600 A * 11/1977 Vit .................................. 424/53
4,672,032 A * 6/1987 Slavkin et al. ............... 435/68.1
(Continued)

FOREIGN PATENT DOCUMENTS

WO    WO 9609028 A1    3/1996
WO    WO 9609029 A1    3/1996
WO    WO0245616 A2    6/2002

OTHER PUBLICATIONS

Peri-implantits Klinge et al., The Dental Clinics of North America, 2005.*

(Continued)

*Primary Examiner* — Heidi M Eide
(74) *Attorney, Agent, or Firm* — Novak Druce Connolly Bove + Quigg LLP

(57) ABSTRACT

A kit having a) a cleaning device, the cleaning device (1) including an elongated base member (2) formed of at least two wires (3) being twisted with each other, and a plurality of bristles (4) fixed between the twisted wires (3) and extending away from the twisted wires (3), whereby the bristles (4) are positioned in a cleaning section (5) at a first end (6) of the base member (2); wherein the bristles (4) consist of titanium or a titanium alloy; and b) a container having a composition including ethylene diaminotetraacetic acid (EDTA) is disclosed. A method for cleaning and/or debriding and/or conditioning a biological mineralized surface and/or a biological soft tissue surface and/or a dental implant is also disclosed. Additionally, there is disclosed a method for preventing and/ or treating a condition in a patient in need of such treatment.

17 Claims, 8 Drawing Sheets

(51) Int. Cl.
*A46B 3/18* (2006.01)
*A46D 1/00* (2006.01)
*A61C 3/00* (2006.01)
*A61C 5/02* (2006.01)
*A61C 8/00* (2006.01)

(56) References Cited

U.S. PATENT DOCUMENTS

| | | | | |
|---|---|---|---|---|
| 5,067,195 | A * | 11/1991 | Sussman | 15/167.1 |
| 6,179,617 | B1 * | 1/2001 | Ruddle | 433/224 |
| 6,343,929 | B1 * | 2/2002 | Fischer | 433/81 |
| 6,379,155 | B1 * | 4/2002 | Riitano et al. | 433/224 |
| 2003/0044752 | A1 | 3/2003 | Fischer et al. | |
| 2003/0099916 | A1 * | 5/2003 | McLean et al. | 433/102 |
| 2004/0158945 | A1 | 8/2004 | Moore | |
| 2004/0214135 | A1 * | 10/2004 | Ruddle | 433/102 |
| 2006/0110709 | A1 | 5/2006 | Clark, Jr. | |
| 2008/0070195 | A1 * | 3/2008 | DiVito et al. | 433/224 |
| 2008/0280260 | A1 * | 11/2008 | Belikov et al. | 433/215 |

OTHER PUBLICATIONS

PCT/EP2010/057786 International Search Report dated Sep. 13, 2010.

* cited by examiner

MEDICAL CLEANING KIT

CROSS REFERENCE TO RELATED APPLICATIONS

This application is a national phase application of, and claims priority to, PCT/EP2010/057786, filed on Jun. 3, 2010, which claims the benefit of priority under 35 U.S.C. §119(b) to European Patent Application No. 0900764.2 filed on Jun. 3, 2009, the disclosures of which are incorporated herein in their entirety by reference.

TECHNICAL FIELD

The present invention relates to the field of cleaning and conditioning of biological and dental implant surfaces.

BACKGROUND OF THE INVENTION

In numerous situations there today exists a need for the cleaning and conditioning of biological and dental implant surfaces. However, currently available methods not always result in a satisfactory result and/or have problems with damaging of tissues or the use of toxic or otherwise harmful agents.

Medical implants are frequently implanted into vertebrate animals today to replace anatomy and/or restore any function of the body.

Dental implants are utilized in dental restoration procedures in patients having lost one or more of their teeth. A dental implant comprises a dental fixture, which is utilized as an artificial tooth root replacement. Thus, the dental fixture serves as a root for a new tooth. The dental fixture is typically a screw, i.e. it has the shape of a screw. The screw is surgically implanted into the jawbone, where after the bone tissue grows around the screw and the screw is fixated in the bone with the bone in direct contact with the implant surface. This process is called osseointegration, because osteoblasts grow on and into the surface of the implanted screw. By means of the osseointegration, a rigid installation of the screw is obtained.

Dental implants are often made of a metal material. Today, all available dental implants on the market are made of titanium, titanium-zirconium or zirconiumoxide/ceramics. Other examples of metal materials commonly utilized for constructing metallic medical implants are steel, titanium, zirconium, tantalum, niobium, hafnium and alloys thereof. In particular, titanium and titanium alloys have proved to be suitable to utilize for constructing dental and other implants. This is due to the fact that titanium is biocompatible, it has excellent corrosion resistance in body fluids, it resists adherence of bacteria, and it is light and strong. Also, titanium shows very good osseointegration behaviour.

Once the dental implant screw is firmly anchored in the jawbone, it may be elongated by attachment of an abutment to the screw. The abutment may, just as the screw, be made of titanium, a titanium alloy, zirconium or a zirconium alloy. The shape and size of the utilized abutment are adjusted such that it precisely reaches up through the mucosa after attachment to the screw. A dental restoration such as a crown, bridge or denture may then be attached to the abutment. Alternatively, the implant screw has such a shape and size that it reaches up through the mucosa after implantation, whereby no abutment is needed and a dental restoration such as a crown, bridge or denture may be attached directly to the screw.

Periodontal diseases are caused by bacteria and toxins in dental plaque, which is a sticky colourless film constantly forming on the surfaces of the teeth. These diseases are very common; it has been estimated that they affect as much as between 70-90% of the world population, and they are the major cause of tooth loss in people over 35 years of age. The most common forms of periodontal disease are gingivitis and periodontitis.

Periodontal disease is, second to tooth decay, the most frequent oral disease and may lead to partial or complete tooth loss. It is caused by bacterial deposits accumulating on tooth surfaces along the gingival margins and results in destruction of tooth-supporting tissues. The destruction of tooth-supporting tissues results in a deepening of the space (periodontal pocket) between the root of the tooth and the gum tissue.

Gingivitis is the mildest form of periodontal disease, causing the gingiva to become red, swollen, and bleed easily. Gingivitis, if untreated, may develop into periodontitis. In periodontitis the infection has progressed to involve the oral tissues which retain the teeth in the jawbone. If untreated, periodontitis ultimately leads to loss of the affected tooth.

Chronic periodontitis, the most frequently occurring form of periodontitis, results in inflammation within the supporting tissues of the teeth, progressive loss of attachment as well as progressive alveolar bone resorption. This form of periodontitis is characterized by pocket formation and/or recession of the gingiva. As the destruction advances, the mobility and movement of teeth increase finally causing spontaneous loss of a tooth or a necessity of tooth extraction.

In patients with implants, periodontitis may develop into a condition called perio-implantitis and is caused by the colonization of bacteria of the implants's surface. The infection may be caused by bacteria introduced during surgery or post-surgically by insufficient oral hygiene. Inflammation in the bone surrounding the implant then causes loss of bone which ultimately may lead to failure of the implant.

Patients with implants are also susceptible of developing a condition called periimplant mucositis. This condition involves the presence of inflammation in the mucosa at an implant but with no signs of loss of supporting bone in contrast to the observed bone loss in periimplantitis patients.

Treatment of periodontal disease usually involves the removal of bacterial deposits and dental calculus. This is commonly performed by scraping the teeth to remove bacterial deposits and dental calculus, including deposits in the gingival margin. However, it is difficult to have full access for treating deeper periodontal pockets resulting in remaining bacteria that may re-infect the tissue. This is of course also the case for other bacterially infected tissues, where an incomplete removal of bacteria or dead or damaged tissue may cause problems for healing and e.g. re-infection. Therefore, this treatment is often combined with surgical procedures to open the tooth pocket to expose the tooth. The roots are then mechanically freed from bacterial deposits and calculus but also granulation tissue and bacterial toxin removal.

It is often advantageous or necessary to debride surgically exposed hard tissue surfaces. For example, debriding of surgically exposed hard tissue surfaces may be advantageous or necessary to perform before regenerative treatment, i.e. in order to prepare the hard tissue surfaces for regenerative treatment. Examples of conditions, which may be associated with a treatment in which debridement of a surgically exposed hard tissue surface is advantageous or necessary to perform in order to prepare the surface for regenerative treatment, are: periimplantitis, periodontitis lesions, marginal periodontitis, apical periodontitis, furcation defects, apical granulomas and cysts, bone cysts, bone tumours, bone granulomas, bone cancers, (infected) extraction sockets, alveolitis sicca ("dry socket"), cleaning of apicectomy defects, localized osteomyelitis, trauma induced defects, resection or revision of implants, resection or revision of fractures, and removal of temporary bone implants.

As mentioned above, peri-implantitis is commonly treated by surgery. Options include debridement, rinsing of the affected tissue and treatment with antibiotics.

It is a well-known fact that the morbidity and frequency of adverse effects, such as e.g. post-surgery effects, are directly related to, and often proportional to, the time used for the debridement of surgically exposed hard tissue surfaces. Thus, rapid debridement treatment ensures a better total treatment outcome. In addition, the total treatment outcome may also depend on the degree of damaging of the anatomical structure by the debridement tool during the debridement procedure. Furthermore, the total treatment outcome may also depend on the amount of contaminating material residues that is left on the treated surface by the debridement tool. Contaminating material residues may trigger a foreign body response.

The surface of dental implants, or the vicinity thereof, has sometimes to be cleaned after placing. This is particularly important when an infection or contamination occurs, causing periimplantitis. In these cases the surface of the ailing implant has to be cleaned from microbes and contaminants to stop the progression of the disease and ensure reintegration of the implant. Failure to clean the implant surface will eventually lead to loss of bone and implant, and make further alternative treatments difficult and sometimes even impossible.

Traditionally, the dentists and surgeons utilize cleaning tools that are relatively hard, i.e. they have a high hardness degree, in order to provide a thorough cleaning of the metallic medical implant during e.g. surgery, implantation or other treatments. Such hard cleaning tools may, for example, be made of stainless steel, hard metal alloys or hard polymers. However, such hard cleaning tools are not suitable to utilize for cleaning all metallic implant materials. For example, they are not suitable to utilize for cleaning medical implants of soft metals or metal alloys, such as e.g. titanium, a titanium alloy, zirconium or a zirconium alloy. This is due to the fact that such medical implants have a delicate surface that may be damaged when contacted by hard cleaning tools. Thus, when hard cleaning tools are utilized for cleaning a medical implant of, for example, titanium, a titanium alloy, zirconium or a zirconium alloy there is a great risk that the surface of the medical implant is damaged by the cleaning process. Then the surface structure of the medical implant is negatively affected. In addition, any produced scratches in the medical implant surface may constitute sites in which bacteria may adhere, which may result in re-infections in the tissue surrounding the medical implant, e.g. the gingiva.

Furthermore, the above mentioned hard cleaning tools may contaminate a delicate surface of a medical implant when utilized for cleaning the medical implant surface, i.e. they may leave contaminating material residues on the medical implant surface. These material residues often trigger a foreign body response and are generally not well accepted by the human body. Also, it is difficult to clean a surface completely with a curette and non-cleaned spots will always remain (see e.g. Schwarz et al., Clin. Oral Invest. (2005) 9: 111-117).

In order to avoid the above mentioned damaging risk, a cleaning tool in the form of a brush comprising soft bristles may be utilized instead of the above mentioned hard cleaning tools for cleaning metallic medical implants having delicate surfaces. The soft bristles may then be made of e.g. a plastic material, nylon or any other synthetic fibers. One example of such a brush for cleaning a dental implant is disclosed in U.S. Pat. No. 6,345,406. However, the cleaning effect of such brushes on the medical implant surface is not as good as that of hard cleaning tools, i.e. it is easier to clean more efficiently and thoroughly by means of hard cleaning tools. In addition, in case such a brush is utilized for cleaning a medical implant surface, it is common that one or more soft bristles, or parts thereof, come loose from the brush and get stuck in the surrounding tissue, e.g. mucosa, whereby inflammation or infections often results.

Etching during periodontal surgery is performed with three main aims: removal of bacterial toxins, removal of smear layer and exposure of collagenous fibres in the root surface and increase visibility through hemostatic effects.

Of these, the two first have been evaluated in vitro employing mainly citric acid and to some extent ortho-phosphoric acid both of which operate at a pH of around 1 (Lowenguth R A, Blieden T M. Periodontal regeneration: root surface demineralization. Periodontology 2000 1993; 1:54).

Scaling and root planing are performed to remove bacterial deposits, calculus and the superficial layers of the root surface (cementum and dentin), structures and tissues which harbour bacterial toxins. Such toxins are not only confined to the bacterial deposits but are also found adsorbed to periodontally diseased root surfaces. These substances have been shown to inhibit cell attachment in vitro, a function necessary for healing. Thus, the aim of scaling and root planing is to provide a biologically acceptable surface for marginal healing. However, following root surface instrumentation, areas of contaminated cementum, as well as a smear layer covering the instrumented surfaces may still remain. Additional root surface treatment, such as etching has been reported to remove the smear layer.

Application of etching agents has been reported to remove smear and debris which may result from scaling and root planing. However, it also may affect the mineralized root surface.

Since its inception citric and ortho-phosphoric acid etching (pH 1) of root surfaces have been reported to result in new attachment or reattachment. In vivo studies have indicated that connective tissue healing with some reparative cementum formation will result after such treatment. There is also reason to believe that application of citric or ortho-phosphoric acid to a periodontal wound during surgery will increase visibility through hemostatic effects as well as facilitate removal of granulation tissue.

As is evident from the above, the cleaning of biological and implant surfaces are difficult and the available mechanical and chemical methods have problems. In conclusion, there is also a need for a cleaning device, which is hard enough to clean/debride well without damaging hard or soft tissue surfaces, which does not leave contaminants on an exposed tissue surface such that a foreign body response is triggered and which may be utilized for relatively rapid cleaning of a soft or hard tissue surface. In addition, there is still a need for improved methods for conditioning the surfaces of hard and soft tissue, and also for the conditioning of medical implant surfaces.

SUMMARY OF THE INVENTION

The object of the present invention is to provide a kit for the cleaning and/or debridement and/or conditioning of a dental implant surface and/or a biological hard or soft tissue surface in order to remove debris, bacteria, toxins and other contaminants on the surface in order to avoid the triggering of a foreign body response, improve wound healing and improve implant attachment and/or acceptability.

This object is achieved by a kit comprising:

a) a cleaning device, said cleaning device 1 comprising:

an elongated base member 2 formed of at least two wires 3 being twisted with each other, and a plurality of bristles 4 fixed between said twisted wires 3 and extending away from said twisted wires 3, whereby said bristles 4 are positioned in a cleaning section 5 at a first end 6 of said base member 2;

wherein said bristles 4 consist of titanium or a titanium alloy; and b) a container comprising a composition comprising ethylene diaminotetraacetic acid (EDTA).

The cleaning device of the present invention is used to mechanically (physically) remove granulose tissue, debris, bacteria, dead or damage tissues etc. from the surface of e.g. a dental implant, hard and/or soft tissue, and/or around the treatment site. Even though the cleaning tool is hard enough to allow removal of the unwanted substances, it is still soft enough to not damage the delicate surfaces of a metallic implant or a hard or soft tissue surface.

The composition comprising EDTA is used for conditioning (etching) the surface of a dental implant and/or a biological hard or soft tissue surface. Such conditioning (etching) e.g. results in the removal of bacterial toxins, removal of smear layers and exposure of collagenous fibres. The EDTA conditioning also prepares an implant surface for reosseointegration. For example, EDTA has been disclosed to functionalize a naturally oxidized titanium substrate that may support the mineralization of the surface (Chuanbin et al., J. Mater. Chem. (1999) 9: 2573-2582).

The combined action of the cleaning tool and the conditioning (etching) effect of the EDTA composition allow an improved removal of unwanted substances on the implant and/or biological surfaces and improves cell attachment, wound healing and/or implant attachment.

The present invention also relates to a kit according to the above for the cleaning and/or debridement and/or conditioning of a biological soft and/or hard tissue surface and/or a dental implant surface and/or to a kit according to the above for use in the cleaning and/or debridement and/or conditioning of a biological soft and/or hard tissue surface and/or a dental implant surface.

In another aspect the invention relates to a method for cleaning and/or debriding and/or conditioning a biological mineralised surface and/or a biological soft tissue surface and/or a dental implant surface, said method comprising the steps of a) cleaning and/or debriding said surface(s) by brushing the surface(s) with the cleaning device as defined above;

b) treating (conditioning) said surface(s) with the EDTA composition wherein steps a) and b) can be performed sequentially or simultaneously.

Another aspect of the invention is directed to the use of the kit for the prevention and/or treatment of a condition selected from periimplant mucositis, periimplantitis, periodontitis lesions, marginal periodontitis, apical periodontitis, furcation defects, apical granulomas and cysts, bone cysts, bone tumours, bone granulomas, bone cancers, (infected) extraction sockets, alveolitis sicca ("dry socket"), cleaning of apicectomy defects, localized osteomyelitis, trauma induced defects, resection or revision of implants, resection or revision of fractures, and removal of temporary bone implants.

Another aspect of the invention is directed to a method for preventing and/or treating a condition in a patient in need of such treatment, said condition being selected from periimplant mucositis, periimplantitis, periodontitis lesions, marginal periodontitis, apical periodontitis, furcation defects, apical granulomas and cysts, bone cysts, bone tumours, bone granulomas, bone cancers, (infected) extraction sockets, alveolitis sicca ("dry socket"), cleaning of apicectomy defects, localized osteomyelitis, trauma induced defects, resection or revision of implants, resection or revision of fractures, and removal of temporary bone implants, said method comprising the steps of a) cleaning and/or debriding and/or conditioning said surface(s) by brushing the surface(s) with the cleaning device as defined herein;

b) treating said surface(s) with an EDTA composition as defined herein, wherein steps a) and b) can be performed sequentially or simultaneously.

Yet another aspect of the invention is directed to the kit for use in preventing and/or treating a condition selected from periimplant mucositis, periimplantitis, periodontitis lesions, marginal periodontitis, apical periodontitis, furcation defects, apical granulomas and cysts, bone cysts, bone tumours, bone granulomas, bone cancers, (infected) extraction sockets, alveolitis sicca ("dry socket"), cleaning of apicectomy defects, localized osteomyelitis, trauma induced defects, resection or revision of implants, resection or revision of fractures, and removal of temporary bone implants.

Another aspect of the invention is directed to the use of the kit for the prevention and/or treatment of a condition selected from the group consisting of: periimplant mucositis, periimplantitis, periodontitis lesions, marginal periodontitis, apical periodontitis, furcation defects, apical granulomas and cysts, bone cysts, bone tumours, bone granulomas, bone cancers, (infected) extraction sockets, alveolitis sicca ("dry socket"), cleaning of apicectomy defects, localized osteomyelitis, trauma induced defects, resection or revision of implants, resection or revision of fractures, and removal of temporary bone implants.

A further aspect of the invention is directed to the kit for the preparation of a medicament for the prevention and/or treatment of a condition selected from periimplant mucositis, periimplantitis, periodontitis lesions, marginal periodontitis, apical periodontitis, furcation defects, apical granulomas and cysts, bone cysts, bone tumours, bone granulomas, bone cancers, (infected) extraction sockets, alveolitis sicca ("dry socket"), cleaning of apicectomy defects, localized osteomyelitis, trauma induced defects, resection or revision of implants, resection or revision of fractures, and removal of temporary bone implants.

Still other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures described herein.

BRIEF DESCRIPTION OF THE DRAWINGS

In the drawings, wherein like reference characters denote similar elements throughout the several views.

DETAILED DESCRIPTION OF THE INVENTION

Figure 1:
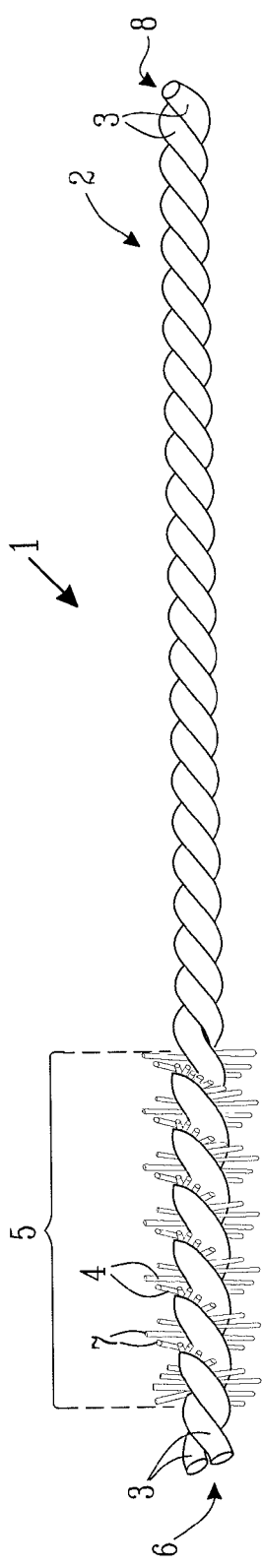
FIG. 1 shows schematically a first design of a cleaning device.

In the present context, the term "dental implant" includes within its scope any device intended to be implanted into the oral cavity of a vertebrate animal, in particular a mammal such as a human, in tooth restoration procedures. Dental implants may also be denoted as dental prosthetic devices. Generally, a dental implant is composed of one or several implant parts. For instance, a dental implant usually comprises a dental fixture coupled to secondary implant parts, such as an abutment and/or a dental restoration such as a crown, bridge or denture. However, any device, such as a dental fixture, intended for implantation may alone be referred to as an implant even if other parts are to be connected thereto. Dental implants may be used to replace anatomy and/or restore a function of the body.

The dental implant is preferably a metallic dental implant or an implant having a metal containing surface. In the present context, the term "metallic dental implant" means a medical implant which mainly comprises metal components, such as implants comprising titanium or a titanium alloy, chromium or a chromium alloy, zirconium or a zirconium alloy, aluminium or an aluminium alloy, tantalum or stainless steel. By "an implant having a metal containing surface" and the like is in the present context meant an implant whose surface in part or fully contains a metal material. For example approximately 10, 20, 30, 40, 50, 60, 70, 80, 90 or 100% of the surface may be made of metal. The structure underlying the implant surface may be made of a metal material or another material, such as a ceramic or polyethylene. The metal material of an implant, independently on whether the full implant or just part(s) of the surface comprises a metal, may e.g. be titanium or a titanium alloy, chromium or a chromium alloy, zirconium or a zirconium alloy, aluminium or an aluminium alloy, tantalum or stainless steel.

Dental implants are preferred implants to be treated using the kit of the invention.

By "etching" is in the present context meant selective removal of part(s) or component(s) from a solid surface through the action of an etching agent, such as an acid solution or other agent. Etching is thus not concerned with erosion of the treated surface to remove a complete surface layer. Etching performed on a root surface in connection with periodontal surgery thus aims at e.g. selectively removing bacterial toxins and hydroxyapatite leaving an exposed layer of collagen. As mentioned above, EDTA treatment of a titanium oxide surface may also support mineralization of the surface (Chuanbin et al., J. Mater. Chem. (1999) 9: 2573-2582). In the context of the present application "conditioning" may also be used to denote the cleaning of a surface, such as a mineralized surface or the surface of an (dental) implant, to remove unwanted substances therefrom, such as e.g. biofilm, bacterial toxins, debris, bacteria, dental calculus (mineralized bacterial deposits) and/or tissue remnants. Conditioning of a tooth surface also includes the removal of hydroxyapatite to expose collagen on the tooth root. "Conditioning" may thus be seen as a cleaning of a surface to remove unwanted substances therefrom and/or prepare the treated surface in order to enable and/or support the regeneration of the surrounding tissue onto the conditioned surface. Etching and conditioning may be used interchangeably in the context of the present invention as in the present context both relate to the removal of unwanted substances from a surface.

The present invention in its first aspect is directed to a kit comprising
a) a cleaning device said cleaning device 1 comprising:
an elongated base member 2 formed of at least two wires 3 being twisted with each other, and
a plurality of bristles 4 fixed between said twisted wires 3 and extending away from said twisted wires 3, whereby said bristles 4 are positioned in a cleaning section 5 at a first end 6 of said base member 2;
wherein said bristles 4 consist of titanium or a titanium alloy; and
b) a container comprising a composition comprising ethylene diaminotetraacetic acid (EDTA).

Alternatively, the composition comprising EDTA may be present on, i.e. applied on, the cleaning device in order to provide a "ready-to-use" cleaning device. The composition comprising EDTA is preferably applied on the area of the cleaning device 1 that comprises the bristles 4.

A kit according to the invention may also consist of said cleaning device and a container comprising said composition comprising EDTA or said cleaning device and said composition comprising EDTA.

The cleaning device of the present invention is used to physically remove debris, bacteria dead or damaged tissues etc. from the surface of a dental implant, preferably a metallic dental implant or a dental implant having a metal containing surface, and/or hard or soft tissue. Even thought the cleaning device is hard enough to allow removal of the unwanted substances, it is still soft enough to not damage the delicate surfaces or a metallic implant or a hard or soft tissue surface.

The composition comprising EDTA is used for conditioning (etching) the surface of the metallic implant and/or a biological hard or soft tissue surface. Such conditioning or etching e.g. results in the removal of bacterial toxins, removal of smear layers and exposure of collagenous fibres. For example, when a tooth root is conditioned with the EDTA composition a conditioning/etching procedure occurs which leaves an exposed layer of collagen on the tooth root. Another advantage with the use the EDTA composition for conditioning is that it avoids toxicological problems. When used on an implant surface, such as a metallic dental implant surface, e.g. a titanium implant surface, in addition the EDTA treatment prepares the implant surface for osseointegration.

Without wishing to be bound by theory, it is envisioned that the mechanical cleaning of a surface using the cleaning device allows the EDTA composition to have a better effect. Alternatively, the cleaning device may provide a better cleaning effect than standard cleaning tools, thereby allowing the EDTA composition to be more effective. By a more effective removal of unwanted substances on a soft or hard tissue or a medical implant surface e.g. the attachment of a loose tooth or an implant may be improved. As demonstrated in Example 1, the combined action of the cleaning device 1 and the EDTA solution of a kit of the invention provides a combined mechanical and chemical debridement that cancel out the surface modifying effects that the cleaning device and the EDTA have on the surface when used alone (See FIG. 10). The use of the kit therefore allows a debridement and conditioning of the surface without a significant modification of the three dimensional structure of the implant surface. It may be important to keep the three dimensional structure of an implant intact, as, as is commonly known in the art, the three dimensional structure may have a great impact on cell attachment also implant attachment in the body.

FIG. 1 shows schematically a first design of the cleaning device 1, i.e. a brush. The cleaning device 1 may be utilized for cleaning a dental implant, preferably a metallic dental implant or an implant having a metal containing surface. Also, the cleaning device 1 may be utilized for the debridement and/or conditioning of biological hard or soft tissue surfaces.

The cleaning device 1 comprises an elongated base member 2, which in the first design is formed of two wires 3 being twisted with each other. However, as will be described below, the elongated base member 2 may alternatively be formed of more than two wires 3 being twisted with each other.

Furthermore, the cleaning device 1 comprises a plurality of bristles 4 fixed between the twisted wires 3. Each bristle 4 extends away from the twisted wires 3, i.e. the length of the respective bristles 4 does not extend in the longitudinal direction of the base member 2. The bristles 4 are positioned in a cleaning section 5, i.e. a brush section, at a first end 6 of the base member 2. The brush section 5 may be positioned in the immediate vicinity of the first end 6 of the base member 2, i.e. with no part of the base member 2 between the first end 6 and the brush section 5. Alternatively, there may be a part of the base member 2 between the first end 6 and the brush section 5 (see FIG. 1). The brush section may have different designs (such as round, cylindrical or conical) especially adapted for different intended uses of the cleaning device, as described further in the below.

The bristles 4 consist of titanium or a titanium alloy. The term "alloy" is herein intended to mean a metallic material containing a base metal and at least one alloying component. The term "base metal" is herein intended to mean the metal being the primary constituent of the alloy and the term "alloying component" is intended to mean a component added to the base metal in order to form the alloy. Thus, the term "titanium alloy" is intended to mean an alloy comprising titanium as base metal and at least one alloying component.

The cleaning device in the kit may also consists of an elongated base member (2) formed of at least two wires (3) being twisted with each other, and a plurality of bristles (4) fixed between said twisted wires (3) and extending away from said twisted wires (3), whereby said bristles (4) are positioned in a cleaning section (5) at a first end (6) of said base member (2);

wherein said bristles (4) consist of titanium or a titanium alloy.

It has surprisingly been found that the cleaning device 1 is advantageous to utilize for cleaning metallic dental implants and/or dental implants having a metal containing surface. It is advantageous to utilize for cleaning both "hard" metallic implants having relatively hard surfaces (including implants having a metal containing surface), such as e.g. medical implants of steel, and "soft" metallic dental implants (including implants having a metal containing surface) having delicate surfaces, such as e.g. dental implants of titanium, a titanium alloy, zirconium or a zirconium alloy. This is due to the fact that the parts of the cleaning device 1 that contact the implant surface in order to perform the cleaning action, i.e. the bristles 4 which are made of titanium or a titanium alloy, have proved to be hard enough to clean both hard and delicate implant surfaces well. At the same time they do not have such hardness that they damage delicate surfaces, i.e. they do not essentially damage delicate surfaces. Consequently, the risk of negatively affecting the surface structure of the medical implant is reduced when the cleaning device is utilized instead of the above mentioned hard cleaning devices. In addition, when the damaging risk is reduced, the risk of formation of scratches constituting bacteria adherence sites is also reduced. Thus, the risk of re-infection in the tissue surrounding the implant, e.g. the gingival, is reduced too.

In addition, the cleaning device 1 does not leave contaminants, i.e. material residues, incompatible with reintegration of the implanted structure. In case a bristle, or parts thereof, come loose, a foreign body response is usually not triggered since titanium is biocompatible. Thus, the inflammation risk due to a loosened piece from the cleaning device is minimal. In addition, a loosened titanium piece may heal up with the medical implant.

In particular, the cleaning device 1 is well-suited for cleaning a dental implant of titanium or a titanium alloy that has a delicate surface, which according to the above is easily damaged by hard cleaning tools. In addition, the titanium or titanium alloy of which the bristles is made may be selected such that the hardness degree thereof exactly, or at least essentially, correspond to the hardness degree of a titanium implant surface to be cleaned. For example, in case the implant to be cleaned consists of pure titanium, it is preferred to select pure titanium as the material of the bristles 4. Alternatively, in case the implant to be cleaned consists of a specific titanium alloy, it is preferred to select the same titanium alloy as the material of the bristles 4. In addition, the cleaning device 1 is also particularly suitable for cleaning a dental implant of zirconium or a zirconium alloy since the hardness degree of zirconium and titanium are similar.

Furthermore, the shape of the cleaning device 1 is well-suited for cleaning a surface of a screw, e.g. a dental fixture having threads, made of titanium, a titanium alloy, zirconium or a zirconium alloy.

The cleaning device 1 may e.g. be utilized during surgery for cleaning of the surface of a metallic dental implant or an implant having a metal containing surface after infection and/or bone resorption. Thus, it may be utilized for removing e.g. bacterial biofilm, debris, calculus and/or fibrous tissue from the surface of a dental implant, such as a titanium screw. Alternatively, the cleaning device 1 may be utilized together with a cleaning agent (i.e. an antibacterial agent) in order to remove the bacterial biofilm from the vicinity of the dental fixture during implantation. The cleaning device 1 may also be utilized for cleaning the surface of, or the vicinity of, an abutment.

In addition, the cleaning device 1 may be utilized for removing cement remnants, bacterial biofilm, debris, calculus or fibrous tissue from the surface of a dental implant.

As mentioned above, the cleaning device 1 may also be used for debridement of biological tissues. More specifically, it has surprisingly been found that the cleaning device 1 may be utilized for other medical cleaning procedures than cleaning or debridement of dental implants. In particular, it is well-suited for debridement procedures, such as e.g. debridement of surgically exposed hard or soft tissue surfaces. For example, debriding of surgically exposed hard or soft tissue surfaces may be advantageous or necessary to perform before regenerative treatment, i.e. in order to prepare the tissue surfaces for regenerative treatment.

Hard tissues are, for example, bone, in particular bone in the oral cavity, such as alveolar bone, teeth, cementum, dentin, enamel, cartilage and ligaments.

The term "debridement" means cleaning of a hard tissue surface in order to remove, for example, biofilm, concrements, microbes, unwanted tissue, cells and cell residues, scar tissue, and/or necrotic tissue. Debridement may, for example, be performed in order to control local infections, inflammations, foreign body reactions, pathological conditions, degenerative processes (e.g. periodontitis or periimplantitis).

Examples of soft tissue to be treated with the kit of the invention include, for example, certinized or nonceratinized gingival tissue, connective tissue, periodontal ligament, epithelium etc.

In particular, it has been observed that the cleaning device 1 is an efficient tool for debridement of surgically exposed tooth root surfaces, furcation defects and bony defects before regenerative treatment (i.e. by means of, for example Emdogain® (Straumann AB, Sweden), bone graft materials, autologous bone, membranes, etc.). The cleaning device 1 is especially effective for removing granulation tissue, and for removing concrements of calcified biofilms (plaques) and subgingival calcus.

The cleaning device 1 is well-suited for debridement of a surgically exposed hard tissue surface, since the parts of the cleaning device 1 that contact the hard tissue surface in order to perform the debridement action, i.e. the bristles 4 which are made of titanium or a titanium alloy, have proved to be hard enough to clean hard tissues surfaces well. At the same time, the hardness, stiffness and elasticity of the titanium or titanium alloy, of which the bristles 4 are made, are such that the bristles 4 efficiently debride the surface without imposing any damage to the anatomical structure, thus maintaining the outline of the original anatomy even after substantial instrumentation of the surface.

In addition, the cleaning device 1 does not leave any biocompromising contaminants on the treated hard tissue surface. Titanium is bio-inert and does not provoke any adverse effects. Any titanium or titanium alloy contamination left on the treated surface does not have any substantial clinical consequence. In case a bristle 4 or part thereof come loose, a foreign body response is usually not triggered since titanium is biocompatible. Thus, the inflammation risk due to a loosened piece from the cleaning device 1 is minimal.

Furthermore, a relatively rapid debridement procedure of surfaces, which are otherwise hard to clean and/or hard to reach by hand instrumentation, may be performed by means of the cleaning device 1. Rapid treatment ensures a better treatment outcome. As mentioned above, it is a well-known fact that the morbidity and frequency of adverse effects, such as e.g. post-surgery effects, are directly related to, and often proportional to, the time used for the debridement of surgically exposed hard tissue surfaces. Thus, rapid debridement treatment ensures a better total treatment outcome.

In addition, the material properties of titanium are such that the tip of the bristles 4 may be manufactured with sharp edges that provide a good "cutting edge" that effectively clean away inflamed/infected soft tissue and calculus from the defect area without harming sound/viable bone or other hard tissues.

The mentioned advantages of the cleaning device 1 imply that when the cleaning device 1 is utilized as a medical debridement tool in a treatment involving debriding of a biological tissue surface, a total treatment outcome is improved.

The use of the cleaning device 1 as a medical debridement tool is especially favorable where the treatment plan for a defect includes placing of a titanium implant or any other device made of titanium, since only titanium and no other metallic ions or polymers that can provoke unwanted (adverse) clinical and/or biological effects can contaminate the treated area, hampering the outcome of planned (future) implant procedures.

As mentioned above, the cleaning device is combined with container comprising a composition comprising EDTA in the kit. The EDTA has a conditioning or etching effect on an implant or a biological soft or hard tissue surface that results in the removal of e.g. biofilm, bacterial toxins, debris, bacteria, dental calculus (mineralized bacterial deposits) and/or tissue remnants. The composition may e.g. comprise EDTA in an aqueous solvent, aqueous matrix or a carrier. Such an aqueous solvent or matrix is advantageous in that it is biocompatible, soluble and possible to easily be washed away. The EDTA may be present at a concentration near or at saturation of the EDTA in such an aqueous matrix or aqueous solvent. The EDTA is preferably present in an aqueous solvent, such as water for injection.

EDTA is an agent which chelates divalent cations, such as $Ca^{2+}$, $Mg^{2+}$, $Fe^{2+}$ and $Pb^{2+}$. It is widely used in infusion solutions for detoxification and as an anticoagulant in vivo. In vitro it has a variety of uses such as to detach cells from solid substrata, decalcification of tissue specimens before sectioning and staining and as a detergent in biochemical analysis.

With conventional etching agents operating at pH 1, not only the mineral component of exposed hard tissue surfaces, such as dentin surface, is dissolved but also the collagenous matrix. Collagen is dissolved at acid pH by acids such as citric acid already at weak concentrations. Thus, EDTA etching in contrast to conventional etching agents will selectively remove hydroxyapatite but not the collagenous matrix of dentin.

EDTA may be used in a photo-masking process to etch a titanium surface. Etching of titanium surfaces may be used to condition the surface for biomimetic hyaluronic acid deposition processes. Also EDTA may be used for functionalizing a titanium oxide surface to support biomineralization (Chuanbin et al., J. Mater. Chem. (1999) 9: 2573-2582).

Preferably, the container comprising the composition comprising EDTA is not a metallic container. Preferably, the container is transparent.

The container the EDTA composition is provided in is preferably a syringe (i.e. the syringe is the container) for easy application to a surface. The volume of the syringe is preferably about 0.5-0.7 ml, more preferably about 0.6 ml.

The volume of the composition comprising EDTA in the kit may be in the range of about 0.05-2 ml, more preferably about 0.1-1 ml, even more preferably about 0.3-0.9 ml. Typically the amount of composition comprising EDTA is about 0.6 ml.

The concentration of EDTA in the composition may e.g. be in the range of about 20-55% by weight, such as about 21-27, 21.6-26.4, 21-55, 26-30, 30-35 or 35-40% by weight. For example, the concentration of EDTA may be about 21.6, 22.0, 22.5, 23.0, 23.5, 24.0, 24.5, 25.0, 25.5, 26.0, 26.4, 27, 28, 29, 30, 35, 40, 45, 50, or 55% by weight. The concentration of EDTA may also be from 20% to 27% by weight, such as about 21, 22, 23, 24 or 25% by weight.

By "weight%", "% by weight", "wt%" and the like is in the present context meant the amount of a solute (by weight) in a solution based on the total weight of the solution, i.e. to be calculated by the formula: (grams solute/grams solution)×100. This means that e.g. a composition comprising 21 g of EDTA in 79 g of water comprises 21 wt % of EDTA. The expression "near saturation" means in this disclosure a concentration which is no less than about 80%, and especially no less than about 90%, of the concentration at saturation.

The EDTA may be present in the composition near or at saturation.

It is preferred that the composition contains water as a major component, and its content of the etching ingredient, EDTA, may be a concentration near saturation or at saturation, such as about 27% by weight based on the water contents of the composition. At around neutral pH the saturation point for the acid, EDTA, lies between about 22 and 27% by weight based on the water contents of the composition, such as about 25%.

Therefore, the composition comprising EDTA may preferably comprise EDTA in a concentration of no less than 80% by weight of the concentration at saturation of EDTA, or more preferably no less than 90% by weight of the concentration at saturation of EDTA.

The composition comprising EDTA may also comprise hydrogen peroxide ($H_2O_2$). Preferably the hydrogen peroxide is provided at a concentration of about 2-4% by weight. For example, the composition may comprise hydrogen peroxide at a concentration of about 2.5-3.5% by weight, such as e.g. about 2.8-3.2% by weight. The concentration of hydrogen peroxide is preferably about 3% by weight. Among other effects, the hydrogen peroxide provides a disinfecting action to the composition as well as it may aid in dissolving proteins and/or removing biological debris. The hydrogen peroxide may also provide an effect of increasing the hydrophilicity of the surface of a metallic implant or an implant having a metal containing surface. In the present invention, hydrogen peroxide rather than a substance being able to give rise to hydrogen peroxide, such as perborate, is used. Perborate, for example, is not water soluble after the reaction giving rise to hydrogen peroxide and a composition with perborate can therefore be difficult to remove after use. In contrast, the composition comprising EDTA used in the kit of the invention is easily removed after it has been allowed to act on a surface by applying water. Also, in the composition comprising EDTA of the kit of the invention, hydrogen peroxide is directly available and ready to act on a surface. Thus a composition comprising EDTA and hydrogen peroxide as disclosed herein allows for short treatment times. The amount of hydrogen peroxide of the composition is high enough to provide for the desired effects, but still low enough to not deteriorate tissue surrounding dental mineralized tissues or dental implants. The hydrogen peroxide may also be provided by way of a peroxide or percarbonate salt, such as sodium peroxide, potassium peroxide, calcium peroxide, or magnesium peroxide. The present inventors surprisingly found that by combining EDTA with hydrogen peroxide in a composition, it was possible to markedly increase the hydrophilicity of an implant having a metal containing surface above what may be achieved when EDTA or hydrogen peroxide are used alone. Thereby, a good hydrophilicity increasing effect may be achieved even with a composition having a lower pH, such as a pH around neutrality. The use of a pH around neutrality may e.g. be advantageous as it decreases the risk that tissue not to be treated by the composition of the invention is negatively affected by composition coming in contact with such tissue, e.g. by dropping or spilling.

The composition comprising EDTA may also comprise a pH controlling agent in order to adjust the pH of the composition. The pH-controlling agent can be any alkaline compound or substance compatible with the intended use of the composition, and the agent may also be constituted by a suitable buffer. The pH of the composition may e.g. be adjusted by the use of any base (i.e. a pH buffering agent) suitable for the intended use of the composition, such as ammonia and hydroxides of alkali metals and alkaline earth metals. Examples include, but are not limited to NaOH, KOH, LiOH, CsOH, RbOH and non-metallic bases such as triethanolamine (Trolamine), diethanolamine, ethanolamine, $NH_3$, phosphates such as $Na_2HPO_4$, $Na_3PO_4$, carbonates ($Na_2CO_3$), and bicarbonate ($NaHCO_3$). Particularly preferred alkaline compounds are sodium hydroxide, potassium hydroxide and calcium hydroxide.

A wide span of pH values of the composition comprising EDTA are possible and the pH of the composition may vary depending on the intended use and/or the desired concentration of EDTA in the composition.

The pH of the composition comprising EDTA is typically about 6-11.5. However, the pH may also be at least 9.0 as further explained below and one example of a composition comprising EDTA is s composition comprising EDTA at a concentration in the range of 21-55% by weight and having a pH of at least 9.0.

In one aspect of the invention, in order to facilitate introduction of the EDTA into the composition it may be preferred to include a pH-controlling agent in an amount resulting in a pH of the aqueous phase of the composition lying within the range from about 6 to about 8, preferably within the range from about 6.5 to 7.5 (i.e. around neutral pH) and even more preferably within the range of pH about 6.5-7.2. It may in some instances be an advantage being able to work around neutral pH during the conditioning with EDTA as the necrotizing effects on surrounding tissues are eliminated in this pH range.

By providing a composition comprising EDTA at a supersaturated concentration (i.e. a concentration where not all of the EDTA is dissolved), it is possible to provide a composition that when used in combination with the cleaning device of the kit of the invention has an abrasive effect on the surface to be treated. The concentration of EDTA necessary to provide such a composition varies with the pH of the composition, with a higher pH enabling a higher amount of EDTA to be dissolved. A composition comprising EDTA at a concentration of about 21-27% by weight and having a pH of 9.0 or above enable a substantial part or all of the EDTA to be dissolved in the solution, thereby providing a composition which contains no or little undissolved EDTA. Such a composition may be advantageous to use as substantially all of the EDTA is dissolved providing a composition having a high concentration of dissolved EDTA. If the EDTA is provided at a higher concentration, such as e.g. about 40-50% by weight, some EDTA remains undissolved. This undissolved EDTA may provide an additional abrasive effect to the composition when used in combination with the cleaning device. For example, plaque may be more easily removed in this way. Such a composition having both a high concentration of EDTA (e.g. about 40-50% by weight) and a pH above about 9.0 has both the advantageous properties of a high amount of dissolved EDTA and an additional amount of undissolved EDTA being able to provide an abrasive effect. Also the hydrophilicity of a metal containing implant surface may be increased when such a composition comprising EDTA and having a pH above about 9 is used for conditioning of an implant surface. A high hydrophilicity of an implant surface is desirable e.g. as this has the effect of accelerating bone and soft tissue regrowth on and around the implant. A kit with such a composition comprising EDTA may thus have the effect of enabling and/or enhancing the osseointegration of an implant when used for cleaning and/or conditioning and/or debriding an implant.

The composition comprising EDTA may preferably be in combination with an aqueous matrix or a carrier or an aqueous solvent. Such a matrix or carrier or solvent is advantageous to use as it is biocompatible.

The composition comprising EDTA is preferably in the form of an aqueous solution. For ease of application of the composition it is preferred that it is in the form of a viscous aqueous solution, wherein the increased viscosity is provided by a viscosity-increasing agent. The composition comprising EDTA may thus also comprise a viscosity increasing agent, such as a polysaccharide, protein or glycoprotein. The composition may thus e.g. take the form of a gel or a semi-fluid material. The use of such a viscosity increasing agent allows a composition of the invention to be applied to a particular site and then essentially stay in place there. Thereby the composition is less likely to "spill", or drip onto an undesired surface, for example a tissue not subject to the treatment, such as the tongue, gums or pallet. This may be advantageous as the composition of the invention is a powerful conditioning composition, which may harm sensitive tissue if not handled with care. By the use of a viscosity increasing agent, it is possible to apply the composition in one place and reduce the risk that the composition reaches surrounding tissue.

The amount of viscosity-increasing agent is typically maximally around 15% by weight typically up to about 5% by weight, such as about 2 to 5% by weight. It may be advantageous to use a lower concentration of viscosity-increasing agent in order to reduce the risk for negative interference of the viscosity-increasing agent with the surface to be conditioned or the EDTA. Preferably the amount of viscosity-increasing agent is about 1 to 5% by weight, e.g. about 1-5, 2.5-5.5, 3-5, 4-5% by weight. The amount of viscosity increasing agent may thus be e.g. about 1.0, 1.5, 2.0, 2.5, 3.0, 3.5, 4.0, 4.5, or 5.0.

The viscosity increasing agent may e.g. be selected from (biocompatible) polysaccharides, proteins, glycoproteins and synthetic polymers. For example, the viscosity increasing agent may be selected from the group consisting of celluloses and derivatives and/or salts thereof, starches and derivatives and/or salts thereof, plant gums, capsular microbial polysaccharides, and algal polysaccharides. Suitable salts of these include any salt that is pharmaceutically acceptable, such as sodium salts.

Among preferred polysaccharides there may be mentioned celluloses and derivatives thereof, e.g. ethyl celluloses, hydroxyethyl celluloses, carboxymethyl celluloses, and salts thereof and starches and starch derivatives, such as hydroxyethyl starch. A particularly preferred viscosity increasing agent is sodium carboxymethyl cellulose or a salt thereof. Among microbial polysaccharides there may be xanthan gum, curdlan, pullolan, dextran, and among algal polysaccharides there may be mentioned agar, carageenans, alginic acid. The concentration of the polysaccharide used in the composition may vary within broad limits but a practical upper limit is about 25% by weight of the polysaccharide based on the weight of the composition. However, much lower percentages may be used and a concentration of the order of up to 10% by weight of the polysaccharide, such as about 1 to about 5% by weight, are practically conceivable.

As an alternative to using a polysaccharide as a viscosity-increasing agent there may be used agents selected from proteins and/or glycoproteins, such as gelatin, denatured structural proteins and proteoglycans.

For example, the composition comprising EDTA comprises, based on the water contents of said composition: EDTA in an amount of about 21 to 27% by weight; sodium hydroxide as a pH-controlling agent in an amount resulting in a pH within the range about 6.5 to about 7.5; and a viscosity-increasing agent constituted by carboxymethyl cellulose (CMC) or a salt thereof in an amount of from about 1% by weight to about 5% by weight. Another example of a composition for such use is one wherein the amount of EDTA is about 25% by weight; the pH of the composition is around neutral, i.e. around pH 7; and the viscosity-increasing agent is sodium carboxymethyl cellulose in an amount of about 3 to 5% by weight.

Another example of a preferred composition comprising EDTA comprises EDTA at a concentration of about 21.6-26.4% by weight and has a pH of about 6.5-7-2. Such a composition is currently sold as "Prefgel™" (Straumann®).

Another example of a composition comprising EDTA is composition comprising or consisting of EDTA at a concentration in the range of 21.6-26.4 by weight, a pH buffering agent in an amount so that the pH of the composition is 9.0-10.5, an aqueous solvent, and optionally a viscosity increasing agent, such as carboxymethylcellulose. Another example is a composition comprising or consisting of EDTA at a concentration in the range of about 21.6-26.4 by weight, a pH buffering agent in an amount so that the pH of the composition is pH of about 9.0-10.0, an aqueous solvent, and optionally a viscosity increasing agent, such as carboxymethylcellulose. Yet another example is a composition comprising or consisting of EDTA at a concentration in the range of about 21.6-26.4 by weight, a pH buffering agent in an amount so that the pH of the composition is ca 9.5, an aqueous solvent, and optionally a viscosity increasing agent, such as carboxymethylcellulose. One example of a composition comprising EDTA having a higher amount of EDTA is a composition comprising or consisting of EDTA in the range of about 40-50% by weight, a pH buffering agent in an amount so that the pH of the composition is about 9.5 or above, an aqueous solvent and a viscosity increasing agent. Examples of suitable pH buffering agents and viscosity increasing agents are described elsewhere herein.

One example of a composition comprising EDTA and hydrogen peroxide is composition comprising or consisting of EDTA at a concentration in the range of about 21.6-26.4 by weight, hydrogen peroxide in a concentration of about 2-4% by weight, a pH buffering agent in an amount so that the pH of the composition is about 6-11.5, an aqueous solvent, and optionally a viscosity increasing agent, such as carboxymethylcellulose. Another example is a composition comprising or consisting of EDTA at a concentration in the range of about 21.6-26.4 by weight, hydrogen peroxide in a concentration of about 2-4% by weight, a pH buffering agent in an amount so that the pH of the composition is pH of about 9.0-10.0, an aqueous solvent, and optionally a viscosity increasing agent, such as carboxymethylcellulose. Yet another example is a composition comprising or consisting of EDTA at a concentration in the range of about 21.6-26.4 by weight, hydrogen peroxide in a concentration of about 3% by weight, a pH buffering agent in an amount so that the pH of the composition is about 9.5, an aqueous solvent, and optionally a viscosity increasing agent, such as carboxymethylcellulose. One example of a composition of the invention having a higher amount of EDTA in combination with hydrogen peroxide is a composition comprising or consisting of EDTA in the range of about 40-50% by weight, hydrogen peroxide in a concentration of about 2-4% by weight, a pH buffering agent in an amount so that the pH of the composition is about 6-11.5, preferably about 9.5 or above, an aqueous solvent and a viscosity increasing agent.

Optionally the composition comprising EDTA does not contain NaOCl.

The kit may further comprise a container comprising a substance for healing soft and/or hard tissue and/or a container comprising a substance for inducing and/or supporting regeneration of soft and/or hard tissue. Two or more substances may also be provided in the same container. Alternatively, the container comprising the EDTA composition may itself further comprise such substance(s). One example of a preferred such substance is one or more enamel matrix derived protein(s).

The enamel matrix is composed of a number of proteins. Examples of enamel matrix derived proteins for use in the kit of the present the invention are amelogenins, proline-rich non-amelogenins, tuftelin, tuft proteins, serum proteins, salivary proteins, ameloblastin, sheathlin, fragments and derivatives thereof, and mixtures thereof. As amelogenins are highly conserved throughout vertebrate evolution, enamel matrix proteins, although of porcine origin, are considered "self" when encountered in the human body and can promote dental regeneration in humans without triggering allergic responses or other undesirable reactions.

Enamel matrix proteins and enamel matrix derived proteins have previously been described in the patent literature to be able to induce hard tissue formation (e.g. enamel formation, U.S. Pat. No. 4,672,032 (Slavkin)), endorse binding between hard tissues (EP-B-0 337 967 and EP-B-0 263 086), promote open wound healing, such as of skin and mucosa, have a beneficial effect on treatment of infections and inflammatory diseases (EPO 1, 1059934 and EPO II, 01201915.4), induce regeneration of dentin (WO 01/97834), promote the take of a graft (WO 00/53197), induce apoptosis in the treatment of neoplasms (WO 00/53196), and facilitate filling a wound cavity and/or tissue defect following from a procedure and/or trauma, such as a cytoreductive surgery (WO 02/080994).

A preparation containing an active enamel substance for use in the present invention may also contain at least two of the aforementioned proteinaceous substances. Moreover, other proteins for use in the present invention are found in the marketed product EMDOGAIN® (Straumann AB, Sweden). EMDOGAIN®, an enamel matrix derivative well known in the art, contains 30 mg Enamel Matrix protein, heated for 3 hours at about 80° C. in order to inactivate residual proteases, per 1 ml Vehicle Solution (Propylene Glycol Alginate), which are mixed prior to application, unless the protein and the Vehicle are tested separately. The weight ratio is about 80/8/12 between the main protein peaks at 20, 14 and 5 kDa, respectively.

The composition comprising EDTA may also consist of ethylene diaminotetraacetic acid (EDTA), an aqueous solvent, optionally a pH controlling agent, optionally hydrogen peroxide, preferably at a concentration of 2-4% by weight, and optionally a viscosity increasing agent.

One aspect of the invention is directed to a kit as described herein for the cleaning and/or debridement and/or conditioning of a biological mineralised surface. The invention is thus also directed to the kit for use in the cleaning and/or debridement and/or conditioning of a biological mineralised surface. The biological mineralised surface may e.g. be an oral mineralised surface, such as a jaw or a dental surface, such as a tooth surface, such as a root canal surface.

Another aspect of the invention is directed to a kit as described herein for the cleaning and/or debridement and/or conditioning of a biological soft tissue surface, such as gingival tissue, connective tissue, periodontal ligament and/or epithelium. The invention is thus also directed to the kit for use in the cleaning and/or debridement and/or conditioning of a biological soft tissue surface Another aspect of the invention is directed to a kit as described herein for the cleaning and/or debridement and/or conditioning of a medical implant surface, in particular a dental implant surface. The invention is thus also directed to the kit for use in the cleaning and/or debridement and/or conditioning of a medical implant surface, in particular a dental implant surface and in particular a metallic dental implant or a dental implant having a metal containing surface.

The kit of the invention may also be used in a method for cleaning and/or debriding and/or conditioning a biological mineralised surface and/or a biological soft tissue surface and/or a dental implant surface. Such a method comprises the steps of a) cleaning and/or debriding said surface(s) by brushing the surface(s) with the cleaning device;

b) treating said surface(s) with the EDTA composition, wherein steps a) and b) can be performed sequentially or simultaneously. Step b) in such a method comprises the conditioning of the surface(s) with the EDTA. Such a method may also comprise the further step of treating the surface with a composition comprising a substance for healing soft and/or hard tissue and/or a container comprising a substance for inducing and/or supporting regeneration of soft and/or hard tissue. Treatment with such a further substance may be performed simultaneously or subsequently to steps a) and b) above.

The brushing may be performed by placing the cleaning device on the surface to be cleaned and/or debrided and moving it over the surface manually or with the help of an instrument for turning it.

The EDTA treatment step is performed by applying the EDTA comprising composition on the surface to be treated with the composition. The EDTA provides a conditioning effect to the surface. Typically the EDTA is allowed to act on the surface for about 10 seconds to about 2 minutes, whereafter it is rinsed from the surface. Preferably the rinsing is performed by the use of water, preferably sterile water, or a physiological salt solution, preferably NaCl.

A procedure involving use of the cleaning device 1 may, for example, involve the steps of: surgically exposing a hard (or soft) tissue surface to be treated; removal of inflamed soft tissue; debriding the surface by means of the cleaning device 1; applying (regenerative/conditioning) treatment as needed; replacing soft tissue; suturing for good primary closure and wound stability; and allowing the wound to heal.

The cleaning and/or debridement and/or conditioning may take place in situ in a subject, such as a human subject, or may take place ex situ, i.e. the conditioning takes place outside the body. The kit may thus be used in situ and/or ex situ. For example, an implant or a loose tooth may be conditioned before implantation or repositioning in a body. An implant may also be removed from the body, conditioned and then repositioned in the body. Alternatively, an implant may be treated using the kit of the invention before implantation.

The kit and method of the invention may be used for the prevention and/or treatment of numerous conditions and in particular for parodental uses. Examples of conditions which the kit of the invention is suitable to treat and/or prevent include infected implants, ailing implants, exposed implants, contaminated implants, or any other condition where implant structures needs debridement to recover normal function in the body. In the below examples of conditions the kit of the invention may be used to prevent and/or treated are mentioned. However, other conditions affecting the oral cavity, including oral soft tissue, oral hard tissue, including teeth and bone structures, and dental implants may also be treated by the kit of the invention. One such example is periodontal disease.

The method for cleaning and/or debriding and/or conditioning a biological mineralised surface and/or a biological soft tissue surface and/or a dental implant surface disclosed above may be used for preventing and/or treating a condition in a patient in need of such treatment, said condition e.g. being selected from periimplant mucositis, periimplantitis, periodontitis lesions, marginal periodontitis, apical periodontitis, furcation defects, apical granulomas and cysts, bone cysts, bone tumours, bone granulomas, bone cancers, (infected) extraction sockets, alveolitis sicca ("dry socket"), cleaning of apicectomy defects, localized osteomyelitis, trauma induced defects, resection or revision of implants, resection or revision of fractures, and removal of temporary bone implants.

The invention is also directed to the use of the kit of the invention for the prevention and/or treatment of a condition e.g. selected from periimplant mucositis, periimplantitis, periodontitis lesions, marginal periodontitis, apical periodontitis, furcation defects, apical granulomas and cysts, bone cysts, bone tumours, bone granulomas, bone cancers, (infected) extraction sockets, alveolitis sicca ("dry socket"), cleaning of apicectomy defects, localized osteomyelitis, trauma induced defects, resection or revision of implants, resection or revision of fractures, and removal of temporary bone implants.

The invention is further directed to the kit for use in the prevention and/or treatment of. a condition e.g. selected from periimplant mucositis, periimplantitis, periodontitis lesions, marginal periodontitis, apical periodontitis, furcation defects, apical granulomas and cysts, bone cysts, bone tumours, bone granulomas, bone cancers, (infected) extraction sockets, alveolitis sicca ("dry socket"), cleaning of apicectomy defects, localized osteomyelitis, trauma induced defects, resection or revision of implants, resection or revision of fractures, and removal of temporary bone implants.

The invention is also directed to the use of the kit for the preparation of a medicament for the prevention and/or treatment of a condition e.g. selected from periimplant mucositis, periimplantitis, periodontitis lesions, marginal periodontitis, apical periodontitis, furcation defects, apical granulomas and cysts, bone cysts, bone tumours, bone granulomas, bone cancers, (infected) extraction sockets, alveolitis sicca ("dry socket"), cleaning of apicectomy defects, localized osteomyelitis, trauma induced defects, resection or revision of implants, resection or revision of fractures, and removal of temporary bone implants.

In particular, the kit as disclosed herein is suitable for use in subjects suffering from periimplantitis. Therefore, the invention is preferably directed to a kit as disclosed herein for use in the cleaning and/or debridement and/or conditioning of surfaces affected by periimplantits and a method of using the kit for the prevention and/or treatment of periimplantitis.

Also, the kit and the method as disclosed herein may be used for the cleaning of extraction alveoles or more generally for the removal of unwanted soft and/or hard tissue.

In the below a number of preferred designs of the cleaning device 1 are given.

The bristles 4 may consist of pure, i.e. unalloyed, titanium. For example, the bristles 4 may consist of titanium selected from the group consisting of: titanium of grade 1, titanium of grade 2, titanium of grade 3 and titanium of grade 4 according to ASTM F67. These types of titanium are sometimes also denoted as "commercially pure" titanium.

Alternatively, the bristles 4 may consist of a titanium alloy, whereby the titanium alloy comprises titanium as base metal and at least one alloying component selected from the group consisting of: zirconium, tantalum, hafnium, niobium, aluminium, vanadium, molybdenum, chrome, cobalt, magnesium, iron, gold, silver, copper, mercury, tin and zinc.

For example, the bristles 4 may consist of a titanium alloy, whereby the titanium alloy comprises titanium as base metal, and aluminium and vanadium as alloying components. One preferred example of such a titanium alloy comprises about 94.5% titanium, about 3% aluminium and about 2.5% vanadium.

The wires 3 may consist of any suitable material, such as e.g. a metal or an alloy. However, the wires 3 consist preferably of titanium or a titanium alloy. Thus, the wires 3 may consist of pure, i.e. unalloyed, titanium. For example, the wires 3 may consist of titanium selected from the group consisting of: titanium of grade 1, titanium of grade 2, titanium of grade 3 and titanium of grade 4 according to ASTM F67.

Alternatively, the wires 3 may consist of a titanium alloy, whereby the titanium alloy comprises titanium as base metal and at least one alloying component from the group consisting of: zirconium, tantalum, hafnium, niobium, aluminium, vanadium, molybdenum, chrome, cobalt, magnesium, iron, gold, silver, copper, mercury, tin and zinc.

For example, the wires 3 may consist of a titanium alloy, whereby the titanium alloy comprises titanium as base metal, and aluminium and vanadium as alloying components. One preferred example of such a titanium alloy comprises about 94.5% titanium, about 3% aluminium and about 2.5% vanadium.

The wires 3 may be solid, i.e. their interior is completely filled up with the unalloyed titanium material or the titanium alloy that they consist of. Thus, they are not hollow.

The bristles 4 and the wires 3 may consist of the same material, i.e. both the bristles 4 and the wires 3 may consist of e.g. pure (unalloyed) titanium of a certain grade or any of the above mentioned titanium alloys. However, the bristles 4 and the wires 3 may also consist of different materials. For example, the bristles 4 may, thus, consist of pure titanium of a certain grade, while the wires 3 consist of pure titanium of another grade. As an alternative example, the bristles 4 may consist of pure titanium, while the wires 3 consist of a titanium alloy, or vice versa. As a further example, the bristles 4 may consist of a certain titanium alloy, while the wires 3 consist of another titanium alloy.

In addition, the respective wires 3 may consist of different materials. For example, one wire 3 may consist of one of the above mentioned unalloyed titanium materials or titanium alloys, while the other wire 3 consist of another of the above mentioned unalloyed titanium materials or titanium alloys. Likewise, one or more of the bristles 4 may consist of one of the above mentioned unalloyed titanium materials or titanium alloys, while the other bristles 4 consist of another of the above mentioned unalloyed titanium materials or titanium alloys.

The base member 2 may have a length of e.g. about 5-500 mm, e.g. about 10-500 mm, 20-400 mm, 100-500 mm, 200-400 mm, or 300-400 mm, such as e.g. 5, 50, 100, 200, 300, 400 or 500 mm. By using such a length of the base member, the brush is short enough to provide the stiffness required to apply the necessary forces to ensure a good cleaning action. The brush area generally has a length between about 3-30 mm. Generally, the shortest length of the brush area is about 3-4 mm, but it may also be shorter if necessary considering the surface to be cleaned. The longest length of the brush area is in general terms about as long as the surface to be cleaned (brushed), but is generally not more than about 25-30 mm. The brush area may therefore be e.g. about 5-20 mm, such as about 8-16 mm, e.g. about 14 mm, or in the shorter range of 3-10 mm, such as about 4-8 mm. The diameter of the respective wires 3 may be e.g. about 0.1-2.0 mm or about 0.1-1 mm. The bristles 4 may have a length of e.g. about 0.1-50 mm or about 0.1-10 mm. The diameter of the bristles may be e.g. about 0.05-1.0 mm or about 0.05-0.5 mm, such as 0.05, 0.1, 0.2, 0.3, 0.4, 0.5, 0.6, 0.7, 0.8, 0.9, or 1.0 mm.

In a first exemplary design of the cleaning device shown in FIG. 1, all bristles 4 have essentially the same length. The outer ends 7 of the bristles 4 form thereby parts of a surface area of a cylinder, whereby the brush section 5 has a cylindrical shape.

The cleaning device 1 may be produced by, for example, any known method in which bristles are introduced between wires, where after the wires are twisted with each other. The bristles 4 may, for example, be fixed between the twisted wires 3 by means of interlocking between the twisted wires 3. Alternatively, the bristles 4 may be fixed by means of electric welding or by means of heating to a high temperature.

The cleaning device 1 may be equipped with a handle at a second end 8 of said base member 2.

Figure 2:
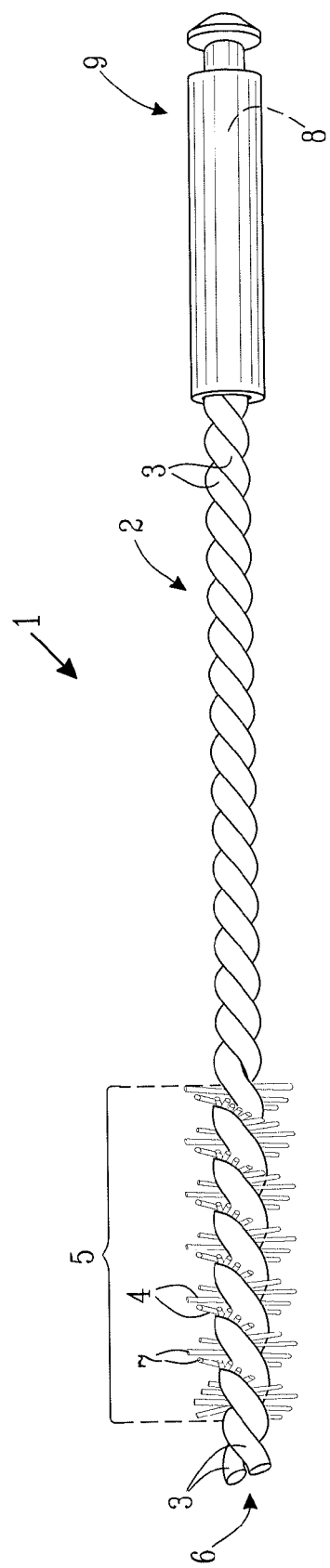
FIG. 2 shows schematically a first design of the cleaning device with a linking component.

Furthermore, the cleaning device 1 may be intended to be utilized together with a motor-driven unit, such as e.g. a contra-angle handpiece for dental drilling or endodontic work, or an orthopedic drill. The cleaning device 1 may then optionally comprise a linking component 9, for connection to a motor-driven unit. The linking component 9 is provided at a second end 8 of the base member 2. FIG. 2 shows schematically a first design of the cleaning device 1 with a linking component 9.

Alternatively, the cleaning device 1 may be intended for manual use. The cleaning device may then optionally comprise a handle (not shown) instead of the linking component 9 at the second end 8 of the base member 2.

The cleaning device 1 in the kit of the invention may also consist of an elongated base member 2 formed of at least two wires 3 being twisted with each other, and a plurality of bristles 4 fixed between said twisted wires 3 and extending away from said twisted wires 3, whereby said bristles 4 are positioned in a cleaning section 5 at a first end 6 of said base member 2, wherein said bristles 4 consist of titanium or a titanium alloy.

Figure 3:
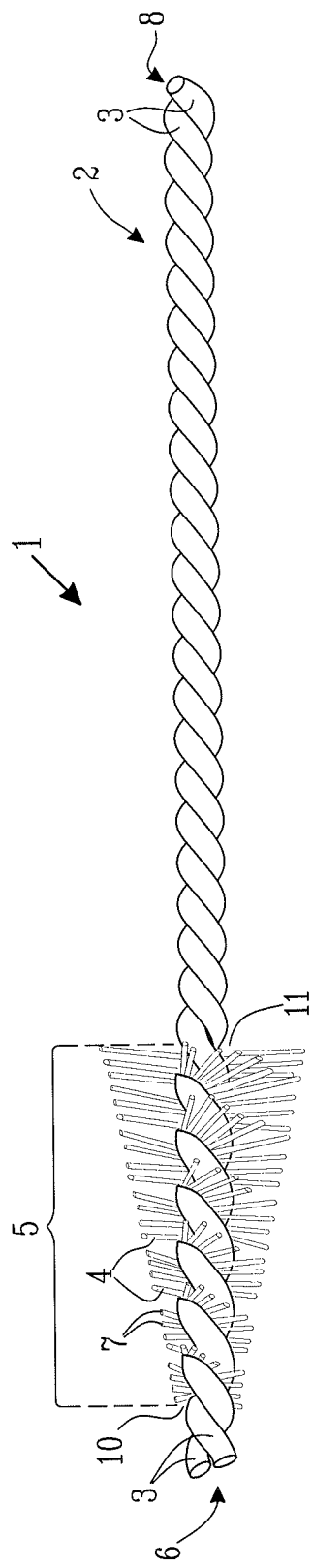
FIG. 3 shows schematically a second design of the cleaning device.

FIG. 3 shows schematically a alternative design of the cleaning device 1. A cleaning device with this design corresponds to the previously described design but differs from it concerning the length of the bristles 4 in that the bristles 4 have a varying length over, i.e. along, the longitudinal direction of the base member 2. More specifically, the bristles 4 have a varying length over the longitudinal direction of the brush section 5. The expression that "the bristles have a varying length over the longitudinal direction" is herein intended to mean that the length of at least some of the bristles 4 is different, i.e. that the length of the bristles 4 differ between at least some positions in the longitudinal direction of the base member 2.

As may be seen in FIG. 3, the length of the bristles 4 of the cleaning device 1 increases successively in a direction from a distal end 10 of the brush section 5 (i.e. a brush section distal end 10) to a proximal end 11 of the brush section 5 (i.e. a brush section proximal end 11). The outer ends 7 of the bristles 4 form thereby part of a surface area of a cone, whereby the brush section 5 has a conical shape.

The design of the cleaning device shown in FIG. 3 may be varied in accordance with the variations of the design in FIGS. 1 and/or 2 and has the same advantages as these. In addition, it has the advantage that the shape is well suited for deep and wide V-shaped pathological bone pockets. This shape will ease the cleaning of these V-shaped pockets.

Figure 4:
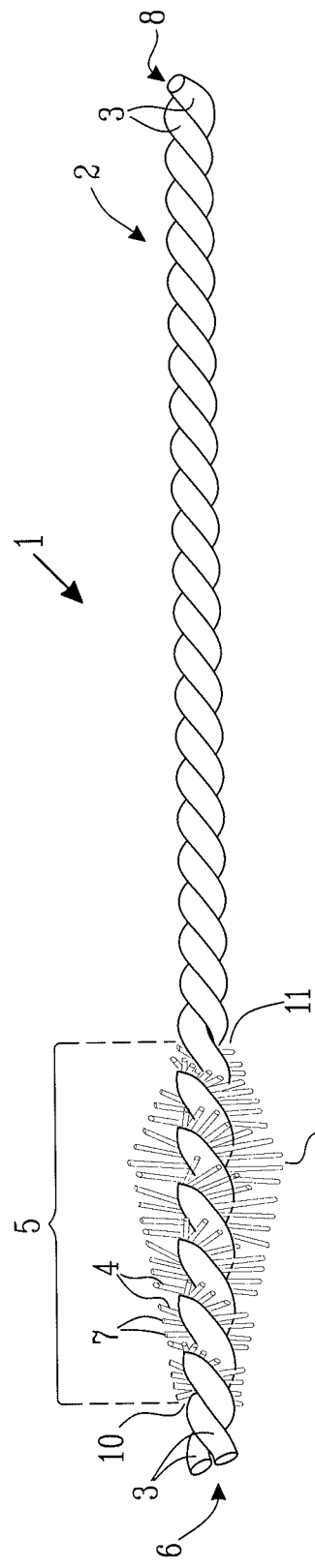
FIG. 4 shows schematically a third design of the cleaning device.

FIG. 4 shows yet an alternative design of the cleaning device 1. This design corresponds to the first design except for concerning the length of the bristles 4 in that the bristles 4 have a varying length over, i.e. along, the longitudinal direction of the base member 2. More specifically, the bristles 4 have a varying length over the longitudinal direction of the brush section 5.

As may be seen in FIG. 4, the length of the bristles 4 of the cleaning device 1 increases successively in a direction from the distal end 10 of the brush section 5 (i.e. the brush section distal end 10) to an intermediate position 12 in the longitudinal direction of the brush section 5. Thereafter the length of the bristles 4 decreases successively in a direction from the intermediate position 12 to the proximal end 11 of the brush section 5 (i.e. the brush section proximal end 11). The outer ends 7 of the bristles 4 form thereby part of a surface area of en element having a diamond-like shape in a side view. Thereby the brush section 5 has a diamond-like shape in a side view.

The design of the cleaning device 1 shown in FIG. 4 may be varied in accordance with the variations of the first design and has the same advantages as the first design. In addition, it has the advantage that the shape is well suited for narrow V-shaped pathological bone pockets which will ease the cleaning of these V-shaped pockets.

In alternative designs (not shown) the bristles 4 have a varying length over the longitudinal direction of the base member 2 such that the outer ends 7 of the bristles 4 form part of a surface area of an element having another shape than those mentioned above.

Thus, the size and shape of the cleaning device 1 may be adapted to a defect anatomy, i.e. the size and shape of the cleaning device 1 may be adapted such that it is suited for debriding of a particular type tissue or implant surface. For example, the cleaning section 5 of the cleaning device 1 may be relatively long and narrow (i.e. the bristles 4 may have a relatively short length), whereby the cleaning device 1 e.g. is suited for debridement of a surgically exposed hard tissue surface in treatment of, for example, vertical periodontics defects. Alternatively, the cleaning section 5 of the cleaning device 1 may be ball-shaped (not shown). Then the bristles have a varying length over the longitudinal direction of the base member, whereby the length of the bristles increases successively in a direction from a cleaning section distal end to an intermediate position in the cleaning section and decreases successively in a direction from the intermediate position to a cleaning section proximal end such that the cleaning section is ball-shaped. A cleaning device 1 having a ball-shaped cleaning section is suited for debridement of a surgically exposed hard tissue surface in treatment of, for example, granulomas and apical periodontal defects. Furthermore, the cleaning section 5 of the cleaning device 1 may have a conical shape (FIG. 3), whereby the cleaning device 1 is suited for debridement of a surgically exposed hard tissue surface in treatment of, for example, wide bone defects, such as marginal periodontal defects and dehiscent defects.

Figure 5:
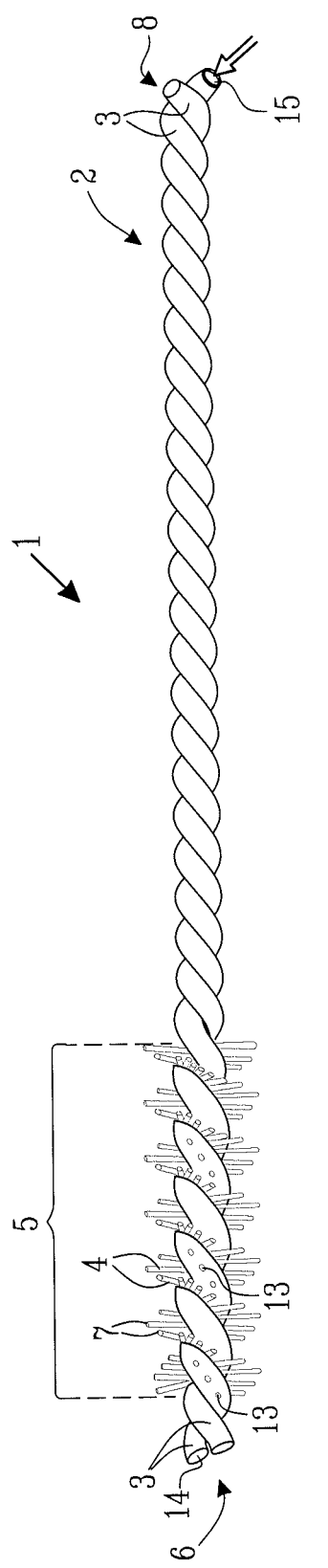
FIG. 5 shows schematically a fourth design of the cleaning device.

Furthermore, any of the above described designs may be varied in that at least one of the wires 3 is a hollow wire comprising apertures in its wall in the cleaning section. FIG. 5 shows schematically a fourth design of the cleaning device 1. The fourth design corresponds to the first design except for the fact that one of the two wires 3 is hollow. The hollow wire 3 is open at a wire proximal end 15 and closed at a wire distal end 14, and comprises a plurality of apertures 13 in the wall of the wire 3 within the cleaning section 5. The hollow wire 3 constitutes a pipe for conducting a fluid from the wire proximal end 15 to its apertures 13 for distribution of the fluid from the interior of the hollow wire 3 along the length of at least some of the bristles 4. Thus, the apertures 13 are positioned so as to constitute apertures for distribution of fluid from the interior of the hollow wire 3 along the length of at least some of the bristles 4. The introduction of a fluid into the hollow wire 3 is indicated with an arrow in FIG. 5. For example, a fluid such as water, sterilized brine, a hydrogen peroxide solution, an antibiotic solution, a weak acid (i.e. maleic acid or formic acid or another weak organic acid) or diluted hydrogen fluoride (0.005-0.1%), may be introduced into the hollow wire 3 during a cleaning operation so as to be distributed along the length of the bristles 4. The fluid may be introduced into the hollow wire 3 in order to irrigate for cooling, for removing debris, for dissolving concrements or mineral precipitations, for flushing the wound and the surface and for killing microbes during cleaning. The fourth design may be further varied in accordance with the variations of the first design. In addition, the fourth design may be varied such that both wires 3 are hollow wires, whereby both wires 3 are open at a wire proximal end 15 and closed at a wire distal end 14 and whereby both wires comprise a plurality of apertures 13 within the brush section 5.

In addition, any of the above described designs may be varied such that the elongated base member 2 is formed by more than two wires 3 being twisted with each other. For example, the base member 2 may be formed by three twisted wires 3. The plurality of bristles 4 are then fixed between the plurality of twisted wires 3.

In case the cleaning device 1 comprises more than two wires 3, one or more of the wires 3 may be a hollow wire corresponding to the hollow wire described in the fourth design. For example, in case the elongated base member 2 is formed by three wires 3 being twisted with each other, two of the wires 3 may be solid and one wire 3 may be hollow. Alternatively, all or at least one of said wires 3 of said cleaning device 1 is a solid wire.

Furthermore, the wires 3 in any of the above designs need not be completely twisted with each other as in the FIGS. 1-5, i.e. parts of the wires 3 at a section at the second end 8 of the base member 2 (at a proximal section of the cleaning device 1) may be untwisted (not shown). Untwisted parts of one or more wires 3 may extend away from the remainder wire/wires 3. For example, untwisted parts of a hollow wire 3 may extend away from the other wire(s) so as to allow convenient attachment to e.g. a fluid source. In addition, the wires 3 in any of the above described designs need not have the same length, i.e. some or all of them may have different lengths. For example, one of the wires 3 may be shorter than the other(s) (not shown) such that the wire proximal end of the shorter wire is located at another position in the longitudinal direction of the base member 2 than the wire proximal end of the other wire(s). In case the cleaning device 1 comprises more than two wires, they may all have the same or different lengths. Alternatively, some of them may have the same length. Thus, in variants of the fourth design shown in FIG. 5, the hollow wire 3 may be shorter or longer than the solid wire 3 and/or extend away from the solid wire 3 so as to allow convenient attachment to e.g. a fluid source.

Another example of a titanium alloy, which the bristles 4 may consist of, is a Titanium-6 Aluminium-4 Vanadium (Ti6Al4V) alloy. For example, the bristles 4 may consist of a Titanium-6 Aluminium-4 Vanadium (Ti6Al4V) alloy selected from the group consisting of a Titanium-6 Aluminium-4 Vanadium (Ti6Al4V) alloy according to ASTM F136 and a Titanium-6 Aluminium-4 Vanadium (Ti6Al4V) alloy according to ASTM F1472.

Alternatively, the bristles 4 may consist of a titanium alloy selected from the group consisting of a Titanium-6 Aluminium-7 Niobium (Ti6Al7Nb) alloy according to ASTM F1295, a Titanium-13 Niobium-13 Zirconium (Ti13Nb13Zr) alloy according to ASTM F1713 and a Titanium-12 Molybdenum-6 Zirconium-2 Iron (Ti12Mo6Zr2Fe) alloy according to ASTM F1813.

Another example of a titanium alloy, which the wires 3 may consist of, is a Titanium-6 Aluminium-4 Vanadium (Ti6Al4V) alloy. For example, the wires 3 may consist of a Titanium-6 Aluminium-4 Vanadium (Ti6Al4V) alloy selected from the group consisting of a Titanium-6 Aluminium-4 Vanadium (Ti6Al4V) alloy according to ASTM F136 and a Titanium-6 Aluminium-4 Vanadium (Ti6Al4V) alloy according to ASTM F1472.

Alternatively, the wires 3 may consist of a titanium alloy selected from the group consisting of a Titanium-6 Aluminium-7 Niobium (Ti6Al7Nb) alloy according to ASTM F1295, a Titanium-13 Niobium-13 Zirconium (Ti13Nb13Zr) alloy according to ASTM F1713 and a Titanium-12 Molybdenum-6 Zirconium-2 Iron (Ti12Mo6Zr2Fe) alloy according to ASTM F1813.

The invention has in part been described with reference to the embodied figures. However, the invention is not limited to the above described designs or embodiments or any other designs or embodiments specifically disclosed. Features from one or more of the above embodiments or variants thereof may be combined as required, and the ultimate scope of the invention should be understood as being defined in the appended claims.

Also, it is to be understood that a kit of the invention may comprise a cleaning device 1 of any herein exemplified design and a container comprising any exemplified composition comprising EDTA, optionally combined with further containers comprising additional substances. In the case the composition comprising EDTA is already provided on the cleaning device 1, any design of the cleaning device 1 may be combined with any composition comprising EDTA disclosed herein.

EXPERIMENTAL SECTION

Example 1

Effect of EDTA-Cleaning Device Kit on the Surface of a Titanium Implant

Titanium implants were fixed in a jig an instrumented with a set force of 500 grams for 2 minutes. After instrumentation the implants were viewed in a scanning electron microscope to look at surface changes.

Figure 6:
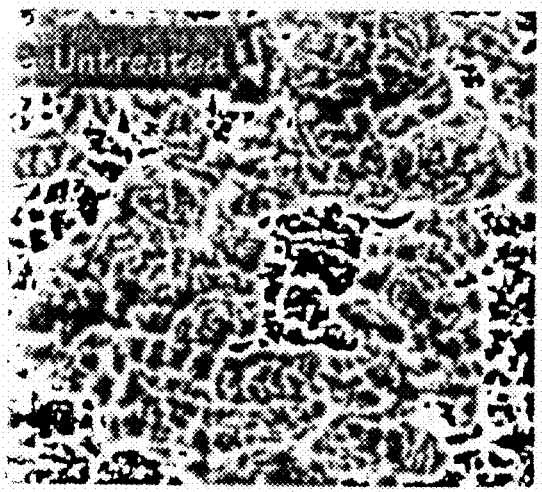
FIG. 6 shows an untreated titanium implant surface.

The untreated implant surface (control) show an anisotropic surface pattern dominated by sharp peaks and deep valleys (FIG. 6).

Figure 7:
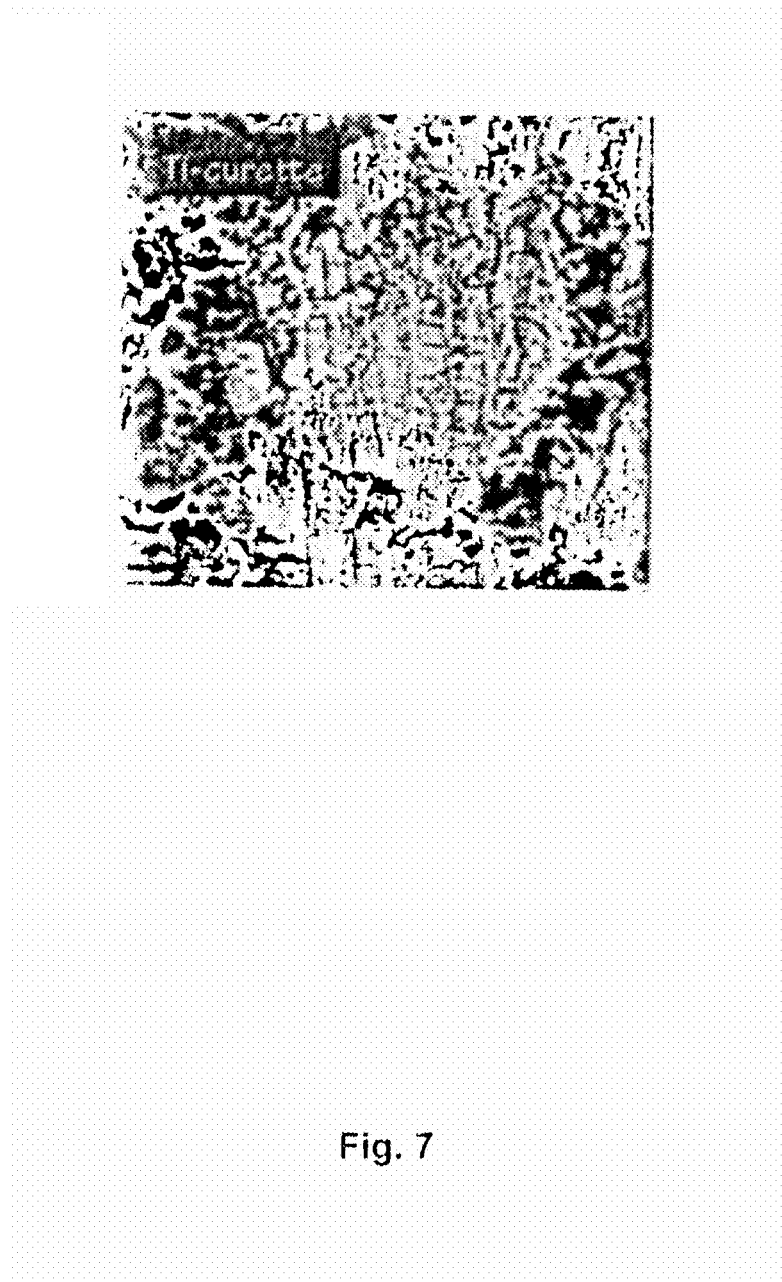
FIG. 7 shows a titanium implant surface treated with Ti curette.

When instrumented with a titanium curette (standard treatment in clinic today) the anisotropic surface is destroyed, showing a surface where areas of the micro-structure has been removed leaving only a smooth titanium surface (FIG. 7).

Figure 8:
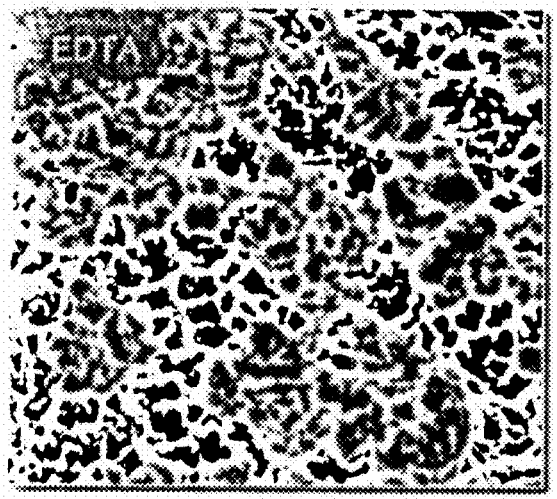
FIG. 8 shows a titanium implant surface treated with EDTA solution.

The untreated surface, when only treated with an EDTA solution (PrefGel, Straumann, Basel, Switzerland) for two minutes, shows no sign of change in the surface anisotropy. However, the micro-architecture shows slightly deeper valleys/higher peaks suggesting that some minor dissolution of titanium ions form the surface takes place (FIG. 8).

Figure 9:
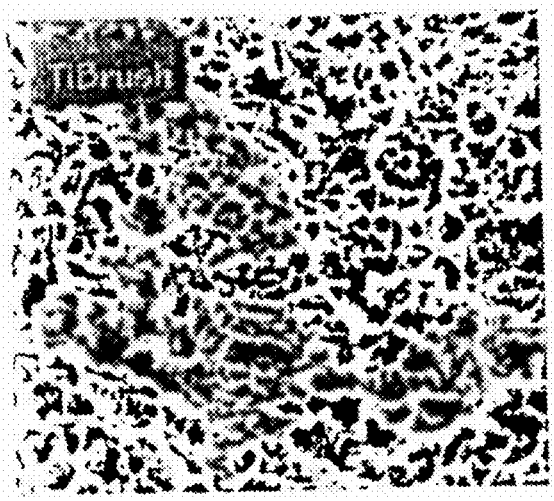
FIG. 9 shows a titanium implant surface cleaned with a cleaning device 1.

When instrumented with a cleaning device 1 made of titanium ("TiBrush"), the anisotropicity and the overall microstructure of the surface is maintained, but the peaks appear flattened with a reduced mean peak to valley distance as a result. There are also small regions where the brush bristles has caused some mechanical damage to the surface, but without affecting the degree of anisotropy or micro-structure significantly (FIG. 9).

Figure 10:
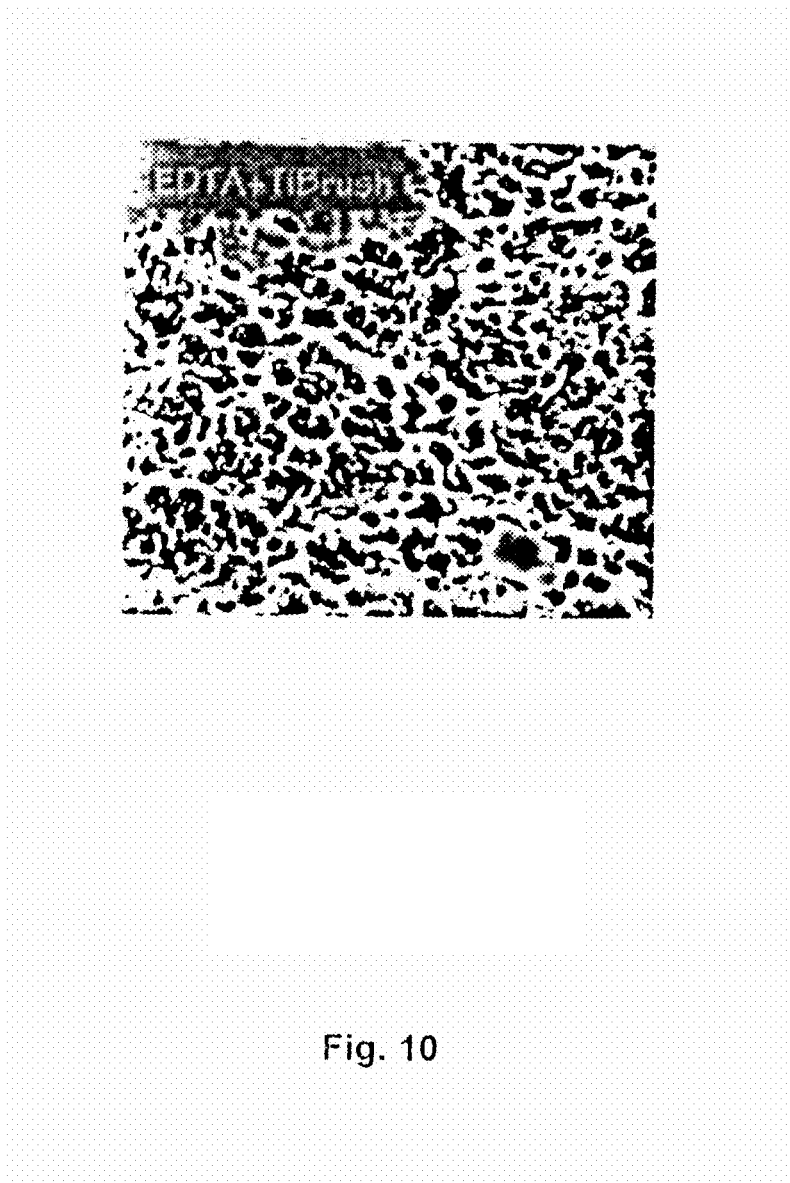
FIG. 10 shows a titanium implant surface cleaned with a cleaning device 1 and conditioned with an EDTA solution.

Surprisingly, when the cleaning device 1 is used together with an EDTA solution (PrefGel, Straumann, Basel, Switzerland) the combined effect of the mechanical and chemical debridement seem to cancel each other out and produce a surface almost identical to the control surface. Therefore, the use of the kit of the invention allows the surface of an implant to be cleaned and conditioned without affecting the three dimensional structure of the implant surface. The cleaning device 1 cleans away and flattens the peak areas, but combined with the dissolution of titanium ions by the EDTA, the majority of peaks remain sharp, and the mean peak to valley distance is maintained (FIG. 10).

The invention claimed is:

1. A method comprising the steps of:
    treating a titanium or titanium alloy surface of a dental implant, the surface having a three dimensional structure adapted for osseointegration to bone, wherein the treating comprising treating with a cleaning device and an EDTA composition comprising ethylene diaminotetraacetic acid in an aqueous solvent to provide a combined mechanical and chemical debridement and conditioning of the dental implant surface without significant modification of the three dimensional structure, comprising steps of:
    a) treating said surface by brushing the surface with a cleaning device (1) comprising:
        an elongated base member (2) having a length of about 10-500 mm between a first end and a second end and formed of at least two wires (3) which consist of titanium and/or a titanium alloy, being twisted with each other;
        a cleaning section having a length from 3 to 10 mm and comprising a plurality of bristles (4) fixed between said twisted wires (3) and extending away from said twisted wires (3), whereby said cleaning section is positioned proximal to the first end (6) of said base member (2), wherein said bristles (4) consist of titanium or a titanium alloy and have bristle diameters of from 0.05 to 1 mm and the bristles have a hardness degree that corresponds to the hardness degree of the titanium or titanium alloy implant surface to be treated; and
        a linking component (9) or a handle is provided at a second end (8) of said base member; and
    b) treating said surface(s) with the EDTA composition, wherein steps a) and b) are performed sequentially or simultaneously.

2. A method for preventing and/or treating a condition in a patient in need of such treatment, comprising the steps of claim 1.

3. The method of claim 2, wherein said condition is selected from the group consisting of: periimplant mucositis, and periimplantitis.

4. The method of claim 1, wherein said EDTA composition comprises ethylene diaminotetraacetic acid (EDTA); an aqueous solvent; and at least one of a pH controlling agent, hydrogen peroxide, and a viscosity increasing agent.

5. The method of claim 1, wherein said cleaning device (1) further the handle comprises the handle the second end (8) of said base member (2).

6. The method of claim 1, wherein the linking component (9) provided at the second end (8) of said base member is configured for connection to a motor-driven unit.

7. The method of claim 1, wherein said EDTA composition comprises EDTA at a concentration near or at saturation.

8. The method of claim 1, wherein said EDTA composition comprises EDTA at a concentration of 20-55% by weight.

9. The method of claim 1, wherein said EDTA composition further comprises hydrogen peroxide ($H_2O_2$).

10. The method of claim 1, wherein said EDTA composition further comprises a pH controlling agent.

11. The method of claim 10, wherein said pH controlling agent is an alkaline compound selected from ammonia and hydroxides of alkali metals and alkaline earth metals.

12. The method of claim 1, wherein said EDTA composition has a pH of at least 9.0.

13. The method of claim 1, wherein the EDTA composition further comprises a viscosity-increasing agent selected from the group comprising polysaccharides, proteins, glycoproteins and synthetic polymers.

14. The method of claim 13, wherein said viscosity-increasing agent comprises carboxymethylcellulose or a salt thereof.

15. The method of claim 1, wherein the method further comprises treating soft and/or hard tissue at the implantation site with a substance for healing, inducing and/or supporting regeneration of soft and/or hard tissue.

16. The method of claim 15, wherein said substance is one or more enamel matrix derived protein(s).

17. The method of claim 1, wherein said EDTA composition comprises, based on the water contents of said composition:
    EDTA in an amount of 21 to 27% by weight;
    sodium hydroxide as a pH-controlling agent in an amount resulting in a pH within the range of 6.5 to 7.5; and
    a viscosity-increasing agent constituted by carboxymethylcellulose or a salt thereof in an amount of from 1% by weight to 5% by weight.

* * * * *

UNITED STATES PATENT AND TRADEMARK OFFICE
CERTIFICATE OF CORRECTION

PATENT NO.        : 9,248,009 B2  
APPLICATION NO.   : 13/322610  
DATED             : February 2, 2016  
INVENTOR(S)       : Fehr et al.

Page 1 of 1

It is certified that error appears in the above-identified patent and that said Letters Patent is hereby corrected as shown below:

In the specification,

In column 1, line 9:

delete "European" and replace with -- Sweden --

In the claims,

In column 26, claim 5, line 12:

delete "further the handle" and insert -- at -- after the text "comprises the handle"

Signed and Sealed this  
Twelfth Day of April, 2016

Michelle K. Lee  
*Director of the United States Patent and Trademark Office*